United States Patent
Martin et al.

(10) Patent No.: US 7,110,107 B2
(45) Date of Patent: Sep. 19, 2006

(54) CAPILLARY ASSAY DEVICE AND METHOD

(75) Inventors: Gregory R. Martin, Acton, ME (US); Allison J. Tanner, Portsmouth, NH (US)

(73) Assignee: Corning Incorporated, Corning, NY (US)

( * ) Notice: Subject to any disclaimer, the term of this patent is extended or adjusted under 35 U.S.C. 154(b) by 396 days.

(21) Appl. No.: 10/741,171

(22) Filed: Dec. 19, 2003

(65) Prior Publication Data

US 2004/0159798 A1    Aug. 19, 2004

Related U.S. Application Data

(60) Provisional application No. 60/435,641, filed on Dec. 20, 2002.

(51) Int. Cl.
*G01N 1/10* (2006.01)
*G01J 3/30* (2006.01)

(52) U.S. Cl. .................................. 356/246; 356/317

(58) Field of Classification Search ............... 356/246, 356/317–319; 422/102, 942; 436/809; 250/458.1, 250/459.1, 461.1, 461.2
See application file for complete search history.

(56) References Cited

U.S. PATENT DOCUMENTS

| | | | |
|---|---|---|---|
| 3,899,672 A | 8/1975 | Levi-Setti | 350/293 |
| 3,926,381 A | 12/1975 | Winston | 350/293 |
| 4,003,638 A | 1/1977 | Winston | 350/293 |
| 4,173,778 A | 11/1979 | Snavely et al. | 362/297 |
| 4,606,636 A | 8/1986 | Monin et al. | 356/338 |
| 5,037,191 A | 8/1991 | Cheng | 359/858 |
| 5,235,470 A | 8/1993 | Cheng | 359/852 |
| 5,675,155 A | 10/1997 | Pentoney, Jr. et al. | 250/458.1 |
| 5,741,412 A | 4/1998 | Dovichi et al. | 204/602 |
| 6,103,083 A | 8/2000 | Merenkova et al. | 204/603 |
| 6,358,387 B1 | 3/2002 | Kopf-Sill et al. | 204/603 |
| 6,387,235 B1 | 5/2002 | Irie et al. | 204/601 |
| 2002/0080349 A1 | 6/2002 | Armstrong et al. | 356/246 |
| 2002/0123073 A1 | 9/2002 | Amirkhanian et al. | 435/7.1 |
| 2002/0179835 A1 | 12/2002 | Feygin | 250/332 |

FOREIGN PATENT DOCUMENTS

| | | |
|---|---|---|
| JP | 2000-019114 | 1/2000 |
| WO | WO 93/07471 | 4/1993 |
| WO | WO 02/059273 | 8/2002 |

*Primary Examiner*—Gregory J. Toatley, Jr.
*Assistant Examiner*—Amanda Merlino
(74) *Attorney, Agent, or Firm*—Joanne N. Pappas

(57) ABSTRACT

A device and method for detecting a signal from an analytical sample is provided. The device comprises a platen with a first and second surface, a number of collection structures extending from the second surface. Each collection structure has a capillary channel running along a common axis as the collection structure from the platen to a terminal end of the structure. Within the capillary channel are sample analytes of interest. On the first surface is disposed a number of optical elements, corresponding to each collection structure, each centered on a capillary channel. Each collection structure has a geometry that can concentrate an optical emission from within the capillary channel, along the entire length of the capillary channel, towards the first surface and optical elements, to a detection device, by means of either mirrored surface reflection or total internal reflection. The collection structure may also direct a light beam into the capillary channel. The present device can be used for non-imaging optical applications from the generated signal.

33 Claims, 14 Drawing Sheets

CAPILLARY ASSAY DEVICE AND METHOD

CLAIM OF PRIORITY

The present Application claims benefit of priority from U.S. Provisional Application No. 60/435,641, filed Dec. 20, 2002, the content of which is incorporated herein.

FIELD OF THE INVENTION

The present invention pertains to a device and method for high-throughput processing and analyzing of biological or chemical assays. In particular, the invention relates to a device and method that improves the transmission and detection of optical signal from a number of low-volume assays, which involve various biological or chemical molecules, tissues or cells currently or formerly in liquid suspension.

BACKGROUND

Biology or chemistry performed on the micro-scale, involving the reaction and subsequent analysis of quantities of reagents or analytes on the order of microliter or sub-microliter amounts, is an increasingly important aspect in the development of new therapeutic agents in the pharmaceutical and other industries. Both to conserve limited samples, reagents, or precious chemical compounds and to increase high-throughput screening capacity, clinical, biological or pharmaceutical researchers often employ reduced-volume assays to detect disease, study biochemical functions, or discover drugs. Several difficulties arise, however, as assay volumes are reduced to microliter and sub-microliter amounts. First, very low volumes of aqueous solutions tend to evaporate rapidly, which causes the concentrations of reagents in solution to change as the amount of water changes. As a consequence, small volume assays often fail to give consistent, accurate results. Second, signals generated from small-volume assays can be imperceptibly low, which may often generate false negative or positive results. Since long exposure times are required for detection of low signal levels by charge-coupled devices (CCD), the ability to process assays quickly with high-throughput capacity is compromised.

The existing technology has relied principally on 96-, 384, or 1536-well microtiter plates containing assay quantities between approximately 0.5 microliter and 0.5 milliliter of liquid compound per well, or involves chemical reactions and analysis in wells disposed with single openings on flat two dimensional surfaces such as glass slides or silicon chips. Unfortunately, these techniques appear to be of moderate success for addressing the issue of evaporation, and of even more limited effectiveness for improving signal detection. A microplate format is not properly configured for efficient collection or direction of an optical signal. The fluorescent signal emitted from chromophores or fluorephores used in biological, biochemical, or chemical assay reactions often is scattered.

Existing microtiter plates passively allow optical signal generated from an assay to escape from the top of the well at random angles with a small percentage of the generated signal being captured by a detector. Fluorescence based assays typically utilize wells with black, light absorbing walls that keep the background from the plate low but have the disadvantage of absorbing the majority of the assay signal. As signal intensity becomes of greater and greater importance as assay volume decreases, these issues become more and more inhibitory to plate performance. Previously, others have tried to address electromagnetic detection of small sample volumes, in particular as relating to capillary electrophoresis systems. Pentoney, Jr. et al., in U.S. Pat. No. 5,675,155, details a system that uses co-planar side-by-side capillaries for sequentially and repetitively scanning a plurality of sample volumes and detecting electromagnetic radiation emitted from each of the sample volumes. Each of the capillaries, oriented in a perpendicular fashion to a mirror reflector, constitutes a single-point radiant source. The system also includes a means for moving and adjusting the mirror's position. This design, however, can not be adapted easily for use with a conventional microplate, and is not compatible with current robotically automated assay processing equipment. The spatial orientation and configuration of the capillaries makes integration with a microplate difficult. That is, one can not merely insert the capillary into a microplate and fill the capillaries. Rather, for the Petoney device to work efficiently with microplates, it appears to require repositioning and various adjustments.

In view of these disadvantages, a new device and method for performing small-volume assays is needed. The new device and method both should be cost-efficient to use and manufacture, efficient for detection, and have high-throughput capability to enable simultaneous mass-volume processing. The present invention can both solve the aforementioned technical problems and satisfies the economic and efficiency needs.

SUMMARY OF THE INVENTION

To reduce evaporative loss as well as improve optical signal detection from an analytical sample, the present invention provides a multi-capillary device for high-throughput screening of low-volume assays. According to the invention, the capillary device comprises: a number of collection structures; a capillary channel, adapted to contain a sample volume, running length-wise along an axis substantially parallel with a major axis of each collection structure; and each collection structure having a shape effective to either concentrate or direct an optical signal from said capillary channel towards a detector. Preferably, the axis of the capillary channel is co-axial with the collection structure. Each collection structure is embodied with a largely solid geometry having a major and a minor axial end, which is adapted to direct an optical signal emitted from an analyte in the sample volume towards the detector by means of reflection, hence incorporating a mirrored surface. The geometry of the collection structure, preferably, incorporates a surface, generated by rotating about an axis, part of at least one of the following: a cone, an ellipse, or a parabola. The radius of rotation can be either of a fixed or variable length. The capillary walls and collection structure are made from a transparent material having an index of refraction that is at least the same, preferably greater than that of the sample volume in the capillary channel.

The device further comprises a planar structure with a first surface and a second surface. The planar structure is situated across the optical aperture or major axial end of the collection structure, which extends in an orthogonal fashion from the second surface. Preferably, the planar structure forms an integral part of the collection structure.

Within each collection structure, the capillary channels are oriented substantially perpendicular to the platen surfaces, and preferably runs along a central axis of each collector. The capillary channel extends through the tapered end or tip of the collector. In some embodiments, the capillary channel may have, in addition to the opening at the terminus of the collection structure, an opening located at the first surface of the planar support structure. Hence, the capillary extends the entire length of the collection structure and support plate. According to such a design, the capillary is open at the tapered end and allows access to sample solutions when the protrusion and channel are inserted into a well of a microtiter plate. The channels are sized to retain a sample volume of liquid in each channel by means of surface tension or capillary action. Hence, each channel may take up into itself sample solutions from a microplate for assays or mixing.

Each capillary channel may have a functionalized interior sidewall surface or be tailored to specific analytical moieties, which may be in the sample. For instance, a functionalized surface or coating in the capillary channel can be useful for affinity capture binding assays for particular biological molecules. Alternatively, for example, the sidewall may be rendered hydrophilic or hydrophobic. Once immobilized within the capillary, biological molecules may serve as probes for biological or chemical assays. One may use the present device to perform virtually any biological or biochemical assays involving fluorescence. For instance, one may employ the present device for monitoring nucleic acid assays, peptide, protein, or lipid membrane assays, or cell culture functions.

In some embodiments, the collection structure has a reflecting surface which has an axis and is open at least one axial end and in an axial section generally conforms to an axial section through a surface generated by rotating a portion of a parabolic curve about an axis perpendicular to the axis of the parabola defined by the curve. The capillary channel forms an elongated source or sink, which extends at least in the direction of the axis of the reflecting surface and is at least partially enveloped by the reflecting surface.

The device further comprises a number of optical elements that are located either within the planar structure or on its first surface, and each of the optical elements corresponds to a collection structure and is centered on the capillary channel. The optical elements can be optical beam-shaping elements, and may include a collimator, such as a lens or microlens (e.g., spherical, aspherical, diopter, fresnel lens of varying focal lengths) or an array of lens or microlenses, which directs said optical signal towards a detector positioned above said first surface, or a reflector, such as a mirror (e.g., concave or convex), which directs the optical signal towards a detector situated below each of said collection structures. Diffraction gratings or surface-relief diffusers are also contemplated. In certain embodiments, the capillary channel may also extend through the optical element. The device is used for non-imaging optical applications.

The present device is adapted for use in conjunction with a conventional microtiter well plate. That is, a collection structure can nest within a well of the plate containing fluid solution, and the fluid solution fills the capillary channel spontaneously by means of capillary action. Because of the smaller cross-sectional surface area of the capillary channel, relative to a microplate well, surface evaporation from within the well is reduced by up to about 10 or about 15 times that of a well not using such a device.

In other aspects, the present invention also relates to a method of using the present device to enable detection of signals from an analytical sample, and a method for its manufacture. The method for detecting a signal from an analytical sample, comprises: a) providing a reflective device for collecting and directing an electromagnetic signal from a capillary channel, adapted to contain a sample volume; b) aligning in a length-wise fashion a linear portion of the capillary channel substantially parallel with a major axis of rotation of the reflective device; providing an analyte in said sample volume; c) optionally introducing an electromagnetic radiation into said capillary channel to induce an electromagnetic emission from said analyte; d) directing said electromagnetic emission toward a detector; and detecting said electromagnetic emission. One may detect using instrumentation suitable to generate signals from the electromagnetic emission, which may include, but is not limited to, charge-coupled devices (CCD), photodiodes, avalanche photodiodes, or photo-multiplier tube (PMT) detectors. The method optionally may further comprise adding a second sample into the capillary channel to react with the first sample; and characterizing the reaction in the capillary in terms of specified assay or chemical properties. The method may further comprise providing or functionalizing the sidewall surface of each capillary channel surface with predetermined properties for engaging biological molecules.

The manufacturing process for the present device is rather straight forward, comprising: a) providing a mold having a predetermined optical-collector geometry, a capillary channel, and optionally an optical element; b) introducing and forming a transparent optical material with said mold; and c) applying a highly reflective outer surface to said collector geometry. The molding surface should have an optical finish on the collection structure, so has to create a polished reflective, mirrored inner surface; polishing the part after fabrication would only give a reflective outer surface, which would not contribute to internal reflection. One may also polish the optical element if it is part of the embodiment. Optionally, one may apply an ant-reflective backing or light-absorbing coating to outside of the collection structure. Optionally, the capillary may be formed by a mechanical or laser drilling, or any method known in the art.

Other features and advantages of the present device will become evident from the following detailed description. It is understood that both the foregoing general description and the following detailed description and examples are merely representative of the invention, and are intended to provide an overview for understanding the invention as claimed.

BRIEF DESCRIPTION OF THE DRAWINGS

In FIG. 13A, the entrance and exit apertures are of radius a and a', respectively. F is the focus of the upper parabola segments, and f is its focal length. The length of the cone is L. In FIG. 13B, the diagram shows the origins and orientations of the focus-centered and symmetry axis-centered coordinate systems.

DETAILED DESCRIPTION OF THE INVENTION

Section I—Definitions

Figure 1:
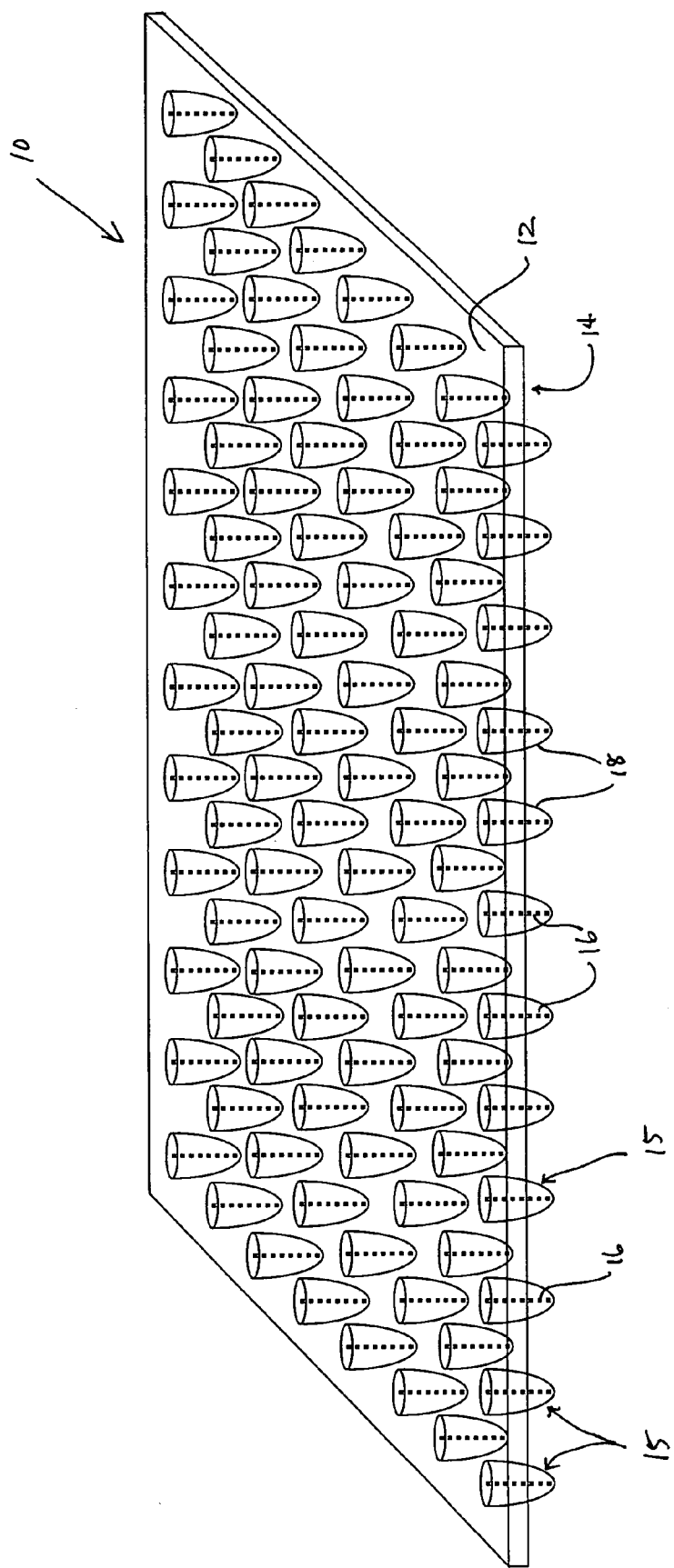
FIG. 1 depicts a schematic presentation of an embodiment of the device according to the present invention. The device comprises a planar support structure having substantially planar first and second surfaces, and a number of collection structures extending away from the second surface of the support. A corresponding number of addressable channels or capillaries traverses through each of the collection structures and, optionally, through the platen to the first surface. Each collection structure surrounds and functions as a reflector or focusing unit for electromagnetic emissions from each capillary channel.

Before describing the present invention in detail, it is to be understood that the terminology used herein is for the purpose of describing particular embodiments only, and is not intended to be limiting. As used in this specification and the appended claims, the singular forms "a," "an," and "the" include plural referents unless the context clearly dictates otherwise.

As used herein, the term "biological molecule" or "biomolecule" refers to any kind of biological entity, including: nucleic acids, such as, modified and unmodified nucleotides, nucleosides, oligonucleotides, DNA, RNA, peptide nucleic acid (PNA); or any kind of amino acids, such as, peptides, polypeptides, proteins, antibodies; or protein membranes, lipids, lipid membranes, or cell membranes; or saccharides, oligosaccharides, or other carbohydrates. The nucleic acid can take the form of either double stranded or single stranded molecules. When a single stranded molecule is used, the nucleic acid can either have a secondary structure or not.

As used herein, the term "ligand" refers to a chemical molecule or biological molecule that can bind readily to a receptor with a specific binding affinity constant.

As used herein, the term "probe" refers to a biological molecule, which according to the nomenclature recommended by B. Phimister (*Nature Genetics* 1999, 21 supplement, pp. 1–60.), is immobilized to a substrate surface. When the array is exposed to a sample of interest, molecules in the sample selectively and specifically binds to their binding partners (i.e., probes). The binding of a "target" to the probes occurs to an extent determined by the concentration of that "target" molecule and its affinity for a particular probe.

As used herein the term "target," or "target compound" as used herein refers to a biological molecule, biochemical or chemical entity, molecule, or pharmaceutical drug candidate to be detected.

As used herein, the term "substrate" or "substrate surface" as used herein refers to a solid or semi-solid, or porous material (e.g., micro- or nano-scale pores), which can form a stable support. The substrate surface can be selected from a variety of materials.

The term "functionalize" or "functionalization" as used herein relates to modification of a substrate to provide a plurality of functional groups on the substrate surface. The phrase "functionalized surface" as used herein refers to a substrate surface that has been modified to have a plurality of functional groups present thereon. The surface may have an amine-presenting functionality (e.g., γ-amino-propylsilane (GAPS) coating), or may be coated with amine presenting polymers such as chitosan and poly(ethyleneimine).

As used herein, the term "complement" or "complementary" refers to the reciprocal or counterpart moiety of a molecule to another. For instance, receptor-ligand pairs, or complementary nucleic acid sequences, in which nucleotides on opposite strands that would normally base pair with each other mostly according to Watson-Crick-base pair (A/T, G/C, C/G, T/A) correspondence.

Section II—Description

A non-imaging device, according to the present invention, provides an exceptionally efficient means for collecting, concentrating, and utilizing electromagnetic energy for biological or chemical assay applications. The present device is adapted to provide increased signal detection by concentrating electromagnetic energy from, preferably, a linear source or sink containing samples in small-volume assays on the order of microliter or submicroliter scale, while also minimizing evaporative loss of the assay medium. Comprehended by the invention are devices including one or more generally conical, elliptical, or parabolic-shaped collection structures having inner reflective surfaces, which function to guide and concentrate radiant energy emitted from a capillary channel, located within each collection structure, containing a biological or chemical sample to be analyzed.

A.—Capillary Device

According to the invention, FIG. 1 depicts, in three-quarter perspective, a schematic view of an embodiment of the present device. The device has a planar support structure or platen 10, with a first or upper surface 12 and a second or lower surface 14, which may constitute part of a lid or cover for a multi-well plate (not shown). A number of protrusions extend in a generally orthogonal fashion from the second or lower surface of the platen. Each protrusion constitutes a collection structure 15, also referred to as a "collector unit," or simply a "collector." Each collection structure has a geometry adapted to collect or direct an electromagnetic radiation signal from a capillary channel 16, adapted to contain a sample volume, towards a detector. Generally, various geometries may be employed to achieve such a phenomenon, including conical, elliptic, or parabolic forms, and other surfaces defined by revolutions about an axis. Preferred geometry of each collection structure incorporates a surface 18, generated by rotating about an axis, which is part of at least one of the following: a cone, an ellipse, or a parabola. According to a preferred embodiment, the geometry of the protrusion can concentrate a section of a linear radiation source to a focal point such that the intensity is an integral along the line of the radiation source, and the light at the focal point behaves as a near perfect, dimensionless source. Conversely, the geometry can map a small point of radiation into a linear sink. Particular suitable geometries will be described further, below.

Figure 2:
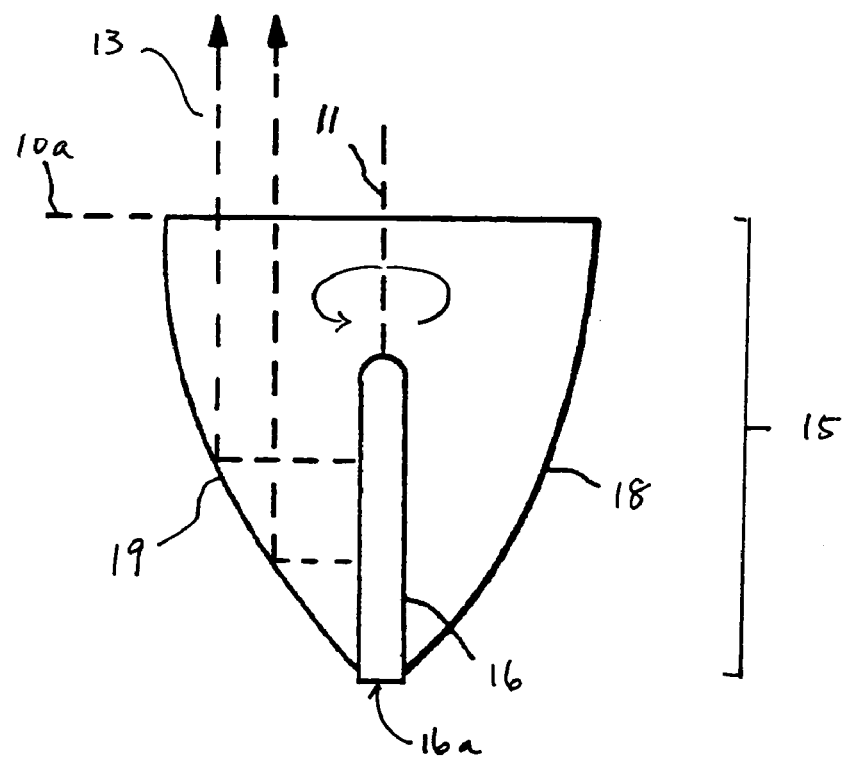
FIG. 2 shows in cross-section an embodiment of an individual collection structure having the geometry of a so-called orthogonal parabolic reflector, with a capillary channel that traverses the body of the collection structure along an axis parallel to a main axis of rotation.
Figure 3:
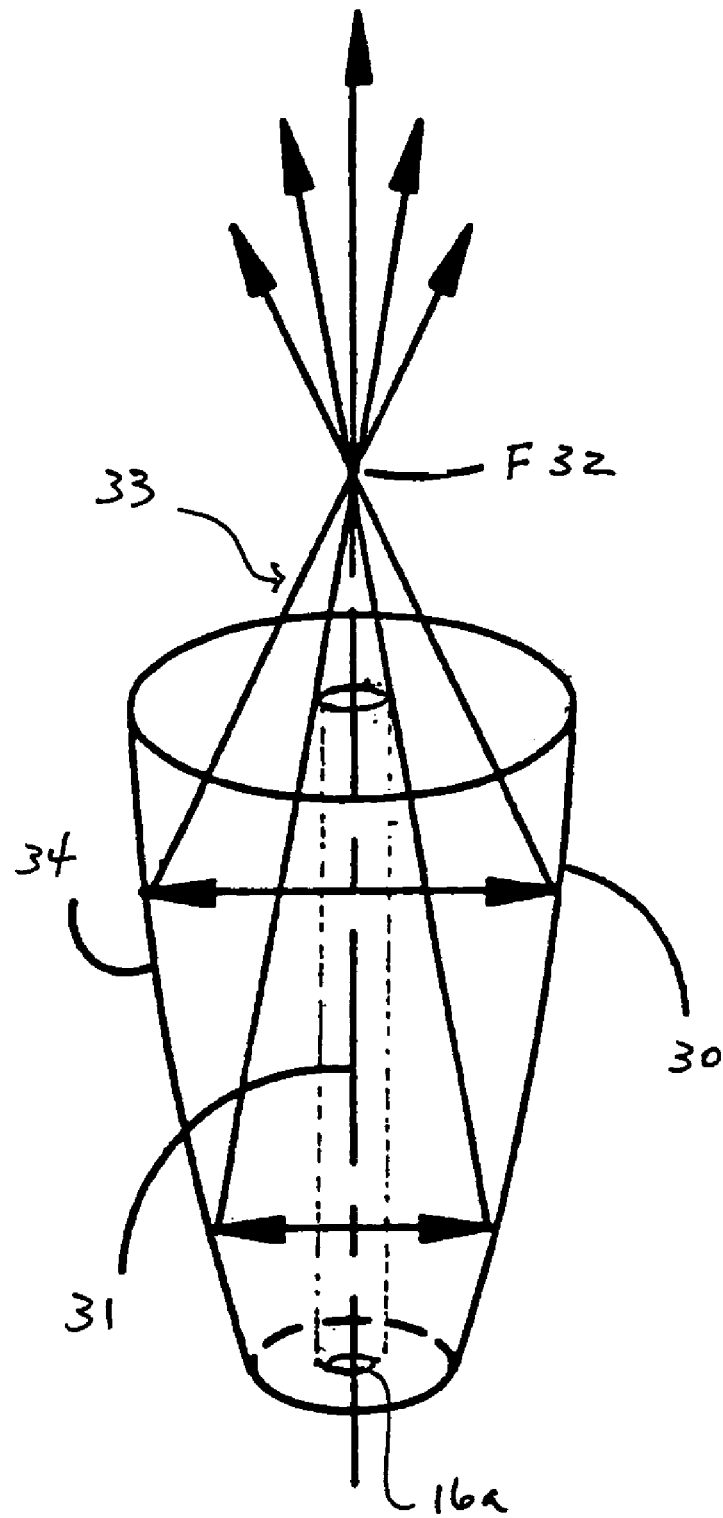
FIG. 3 depicts an isometric view of another embodiment, with a number of emitted light rays converging on a focal point F.

FIG. 2 presents an enlarged cross-sectional view of an individual collection structure 15 according to an embodiment having a parabolic geometry centered about an axis of rotation 11. FIG. 3 is an isometric view of an embodiment having a parabolic or an elliptical geometry, accompanied by a number of ray tracings 33, which converge on a focal point F at 32. The surface 18 generated by rotation has a highly reflective surface-coating 19 that enables it to gather and direct optical radiation 13 either into or out from the capillary channel 16. The reflective surface 19 may have a layer of a reflective material, with an over-coating of a dark backing that dampens or avoids optical cross-talk between adjacent collector structures. The plane at 10a may constitute either the upper or lower surface of the platen, depending on particular embodiments that may incorporate optical elements.

Figure 11:
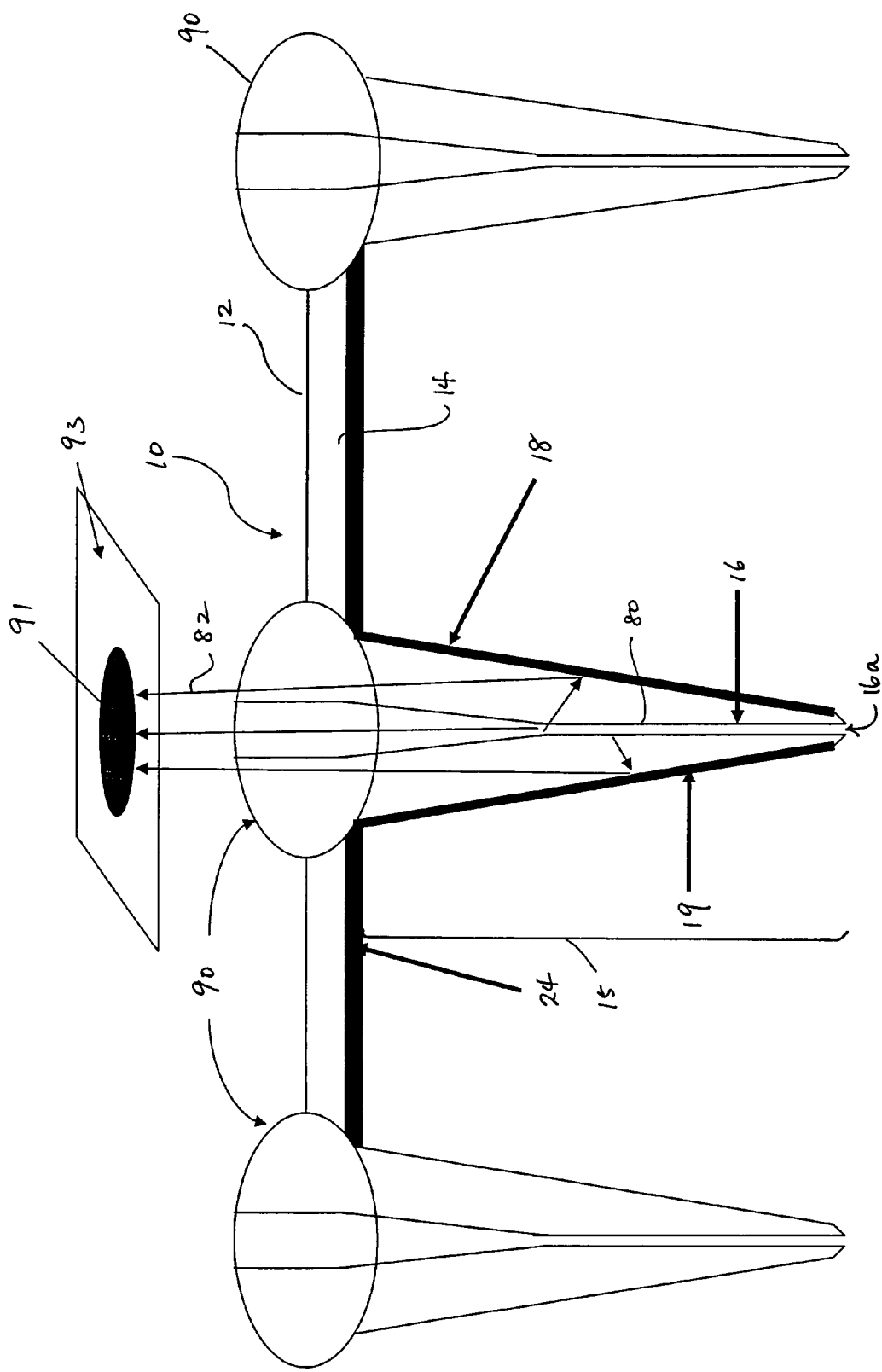
FIG. 11 is a represents in cross-section an alternate embodiment of the invention showing three collection structures with a conical shape, and their associated optical elements.
Figure 12:
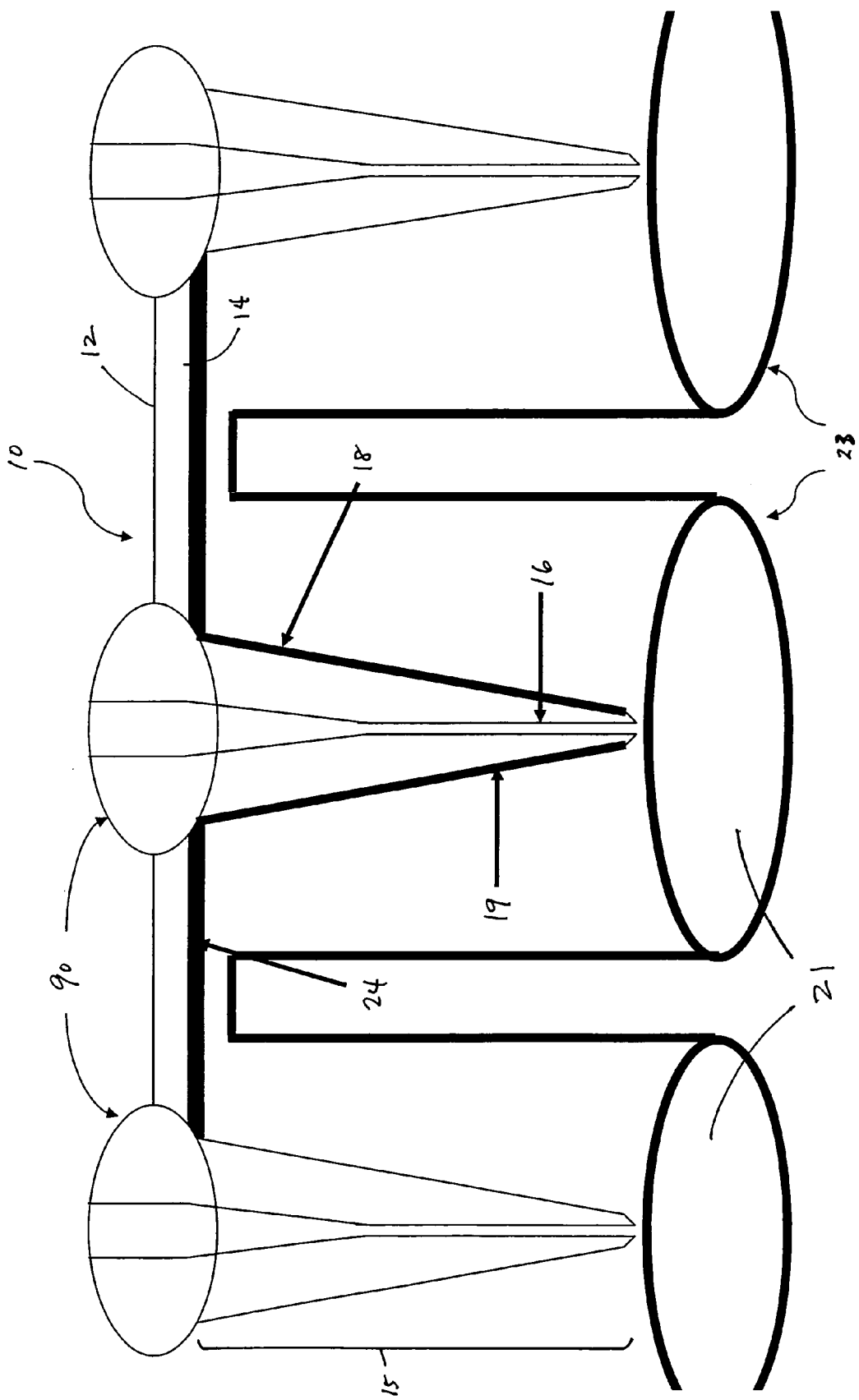
FIG. 12 illustrates a way according to the invention by which the embodiment of FIG. 11 may be used, when the planar support forms part of a lid of a microtiter, multi-well plate. Each collector unit and capillary fits within a corresponding well when inserted.

In preferred embodiments of the device, the platen structure and/or its first surface may include a number of optical elements 90, such as lenses or microlenses, reflectors or mirrors, or gratings to shape or redirect the optical signal, such as illustrated in FIGS. 4, 5, 6, and 7. In other words, optical elements may be located either within the planar structure, or partially within and extending partially outside the platen, or only as a surface feature. Alternatively, the platen may be devoid of any optical elements either within the platen or on its first surface, leaving the first surface of the platen smooth and flat. In such situations, the collection and redirection of a light beam most likely will rely on optical elements within the detection device itself The capillary channel 16 in each collection structure 15, preferably, is oriented orthogonally to the plane of the platen support structure 10, and runs along an axis substantially parallel with the major axis of rotation of each collection structure. Preferably, the capillary channel is co-axial with the central axial core of each collector. The body of the collection structure forms and defines the sidewalls 80 of the capillary channel. The capillary channel, according to certain embodiments, such as shown in FIGS. 11 and 12, may run from the first surface of the platen 10 through the thickness of the platen to a remote end of the collection structure 16a. Hence, the capillary channel within the collector may have a length longer than the collection structure itself.

The surface chemistry of the sidewall 80 in each capillary channel may be functionalized to permit selective binding of biological molecules. A functionalized surface or coating with desired properties applied to the inner wall surface of each capillary channel can be either binding or non-binding based on the particular use or assay procedure. For instance, the coating may have an affinity for molecules, such as proteins, antibodies, toxins, small molecules, carbohydrates, pharmaceuticals, or other biological or chemical moieties. This kind of treatment simplifies assays that rely on surface affinity for immobilizing molecules of interest, followed by washing to remove unbound molecules. For example, bound biomolecules could serve as a mechanism of a purification step, in a manner similar to chromatography or affinity columns, or function as a capture molecule for solid phase assays, such as antibody-antigen or receptor-ligand specific capture. Alternatively, solid phase extraction can be performed by functionalizing the capillary surface with various chemistries that would enable binding through ionic or hydrophobic interaction, or metallic or covalent bonds. Optionally, the capillary may be filled with a porous solid to increase surface area available for binding while maintaining the capillary properties. The surface of a porous solid may further serve as a substrate for growing cells.

The platen, each collection structure, its associated capillary channel, and optical elements may be fabricated from a variety of materials. The plate can be made from any solid or semi-solid (i.e., porous) material. In accordance with various embodiments, the platen may be made from metal, semiconductor, glass, quartz, ceramic, or polymer materials, without limitation by way of example, as long as the material prevents liquid and optical cross-talk between individual capillary channels. The collection structure and capillary channel can be made of materials like those permissible for the platen, as long as the material is transparent, and preferably has minimal or no background auto-fluorescence at the wavelength of interest. Inorganic materials, such as glass, glass-ceramics, or fused silica, which have properties for light transmission or optical waveguiding, or organic materials, such as optically clear polymers or plastics of uniform index having functional groups that do not generate a high background auto-fluorescence at interrogation wavelengths or scatter centers from crystallite phase separations are preferred. For instance, the optical plastic may be selected from particular types of polystyrenes, polypropylenes, acrylates, metharcylates, polycarbonates, polysulfones, polyester-ketones, poly- or cyclic olefins, polychlorotrifluoroethylene, polyethylene terephthlate, or polymer compositions such as described in U.S. Pat. No. 6,653,425, U.S. Pat. No. 6,166,125, U.S. Pat. No. 6,593,415, or U.S. Pat. No. 6,590,036, incorporated herein by reference. In manufacture, one may use thermally extrudible or moldable optical plastics that avoid incorporation of brighteners or whitening reagents. Alternatively, after fabrication, the various material surfaces and may be treated with a reducing agent, such as a borohydride (e.g., $NaBH_4$), to remove background signals.

According to another embodiment, the capillary channel can be formed from light-guiding, flexible, fused-silica capillary tubing, such as commercially available from Polymicro Technologies, Phoenix, Ariz., coated with a cladding of index appropriate material for internal reflection. Fused-silica capillary tubing can provide unique sample detection and analysis applications, including increased path-length detection cells, evanescent wave optics, guiding fluorescence emissions from capillary tip, monitor emission from ligands bound to capillary internal surface. Ultraviolet transmissions inside the capillary can initiate light-activated chemistries, or be used to detect light producing reactions.

B.—

To facilitate detection purposes, as mentioned before, a number of optical beam-shaping elements may be located either within the platen or on its first surface. The optical elements correspond to each collection structure, such that preferably, each optical element is centered on a capillary channel, as is illustrated in the various accompanying figures. The optical elements may include optical filters, gratings or surface-relief diffuser, reflectors (e.g., mirror), collimators, or focusing elements, such as a lens or microlens (e.g., fresnel, convex, concave, diffractive (binary, non-binary) lens), or an array of lenses or microlenses. The optical elements can concentrate, coalesce, and collimate the photo-luminescence emitted from the assay samples within each capillary to enhance light signal detection. The beam-shaping element can either collimate or concentrate light emitted from a sample. The beam-shaping element may take the form of a transmissive optical constituent, such as a lens. In another embodiment, such as in FIG. 8, the optical element can be a reflective unit to redirect emitted signal towards an optical detector.

Alternatively, the optical elements can not only direct the signal generated within the capillary to a detection device, but in the case of fluorescent detection, also can direct excitation illumination into the capillary volume. Without moving the capillary or the electromagnetic radiation source, the detection instrument can focus effectively an excitation wavelength to fluorophore labels on analyte moieties (e.g., peptide or protein molecules, or cells or cellular components) in the assay and can then effectively collect the emission wavelength generated from these labels, allowing for sequential and repetitive detection of samples within the volumes by a single detector. The light beam could be coupled or other wise introduced down the length of the capillary, which would function much like in an optical fiber.

The geometry of the collection structure in the present invention directs the excitation radiation to each capillary, without moving the capillary or moving the radiation source, hence no bulky system of components is required. Unlike the system described in U.S. Pat. No. 5,675,155, which employs a single-point emission source, the present invention uses a linear source, which involves a more complicated optical design since optical parameters are significantly different from a single-point radiant source. Emitted electromagnetic radiation from the sample volume is collected and directed to a detector or an array of detectors, where a signal is generated in response to the interaction of the electromagnetic radiation with the sample and can be analyzed according to standard optical techniques.

Figure 9:
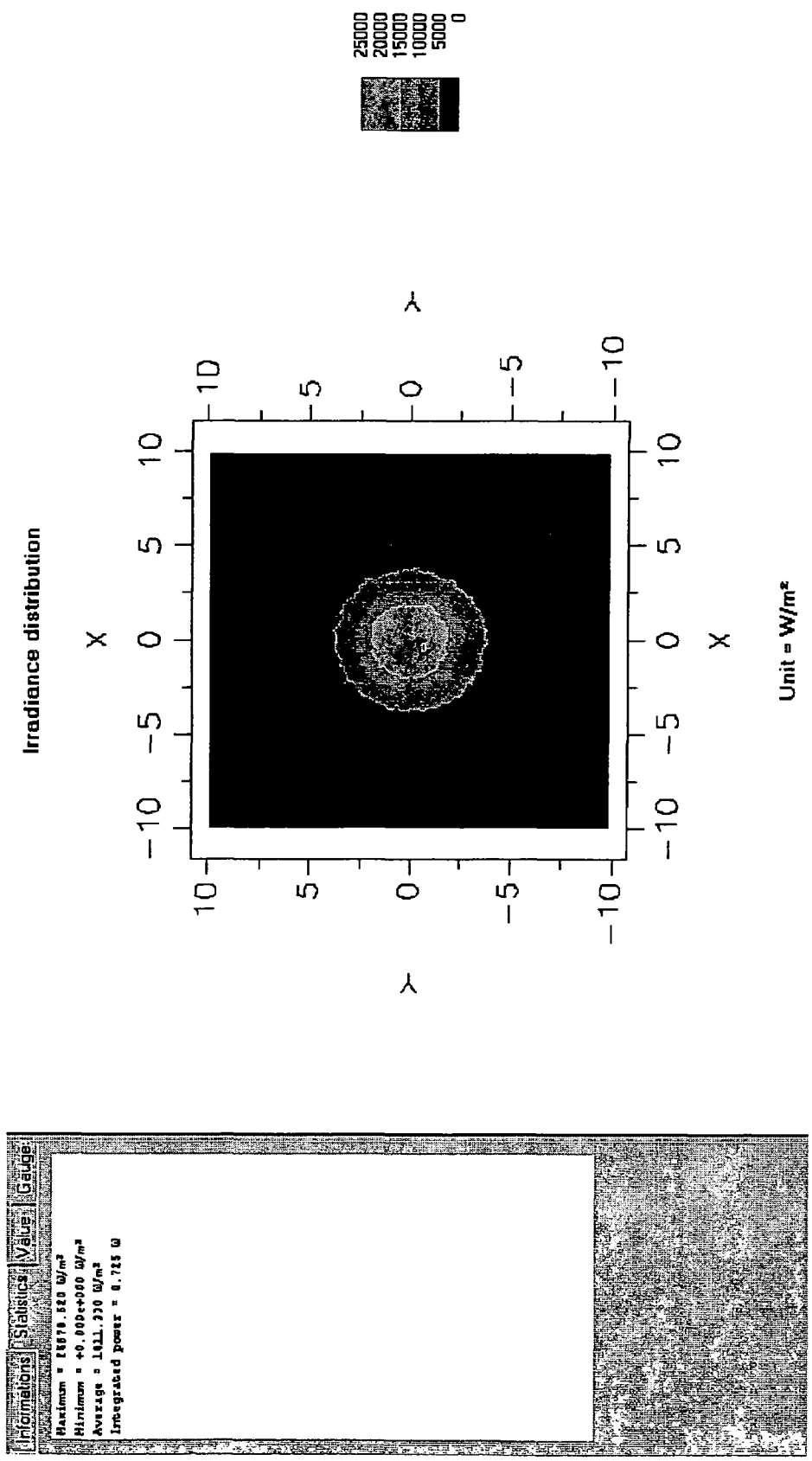
FIG. 9 shows the irradiance distribution on a screen as projected from the paraboloid collection structure of FIG. 8.

The device employs an example of non-imaging optics, where one does not form an image, but simply collects the relative signal from each portion along the length of the capillary. The entire signal from a capillary can be imaged as a concentrated signal spot, versus a diffuse, spreading cone of light. FIG. 9 depicts one such spot for an illustrative example under artificial coloration. Fluorescence emitted from an analyte in the capillary channel is collected and delivered to a detection device. Projecting the signal from the capillary out to the detector, one observes a light spot with a concentric, gradient of relative intensity over the radius of the spot. As a preferred use is a non-imaging application, the gradient of intensity is unimportant so long as the detector can collect it all (or as much as possible). To maximize light flux onto a detector at a distance of a few centimeters, the collector structure must gather the light from the capillary (i.e., cylindrical isotropic source) and form a collimated beam. One wants to conjugate optically the focal point of the conic well with a point, which is ideally at infinity. For these types of problems, the shape of the reflective surface is preferably parabolic or elliptic.

CCD or PMT detectors, for example, or other signal capture devices familiar to those of the art, may be used to convert photons from of the assay into electrical signals. With a CCD imager or PMT detection device incorporated with a CCD one can capture the actual image of the signal spot and digitally convert the baseline intensity to a density of photons to generate a three-dimensional image. The detector can have a set of optical elements, such as either a series of lenses, each with a different focal length, or a compound lens structure, or one can vary the distance between the detector and the device, so as to capture as much emitted signal as possible, particularly if an embodiment of the inventive device itself does not include optical elements.

To facilitate detection of optical signal emitted from a sample in the capillary channel, each collector has a three-dimensional form and surface properties that optimize concentration of the light signal. According to an embodiment, a light ray emitted from an analyte sample is bounced off of a reflective surface of the collector structure, projected toward the first surface of the platen, and transmitted through a beam-shaping optical element to the detector. Configuration of the angles of the side wall or the surface curvature of the protrusions extending from the second surface, along with the air-liquid-substrate-material interfaces, increases the percentage of signal light, which is detectable when the signal exits through the top surface of the device. Superior optical sampling of the volume of the capillary channel may be obtained if the capillary has a more uniform, circular cross-section, and if the radiation is guided by the walls of the capillary channel like that of a waveguide, while the body of each collection structure functions as light reflectors. The material of the collector has an index of refraction that is preferably either the same or higher than that of the material in the capillary channel. Each collector preferably has a highly reflective or mirrored surface 19 formed of a metal coating, such as a layer or film of silver, nickel, aluminum, chromium, or gold, to help direct electromagnetic radiation emissions toward an optical element and ultimately a detector unit. If a feature to polarize the optical signal is desired, a dielectric layer or coating may also be added to the device.

Previously, the aspect ratio of microliter volumes of fluid in microplates with sidewalls decreases the amount of signal that can be captured by CCD and PMT detectors. In contrast, with the present invention, the angle of surface curvature of the collector structure, along with their air/polymer interfaces, increases the percentage of signal light (generated in an assay) that exits through the top of the lid to be captured by a detector. This occurs because the capillary wall acts as a limited waveguide. A lens or other optical element at the top of each collector acts to collimate the signal light and enhance signal detection. Depending upon the angle of curvature of the projections, signals generated from the solutions within the capillaries will be detected from the optical element instead of from within a microwell, thus decreasing shadowing and absorbance by the sidewalls of the wells. Throughput may also be enhanced because the increased signal intensity can lead to a decrease in exposure time for CCD detectors.

An example of the utility and virtues of the present invention is illustrated by calculations derived from a 0.020 inch capillary in a collection structure with a conical angle of about 6.8° from normal. The calculations indicate that the device, through total internal reflection, can increase the amount of signal leaving the capillary by about 8.9 times relative to a 1 µL in a 1536-well "black body" plate (17.8% vs. 2%). Metallizing the projections would greatly enhance this effect by creating a highly reflective surface 19. Also, a metal coating can permit the capillary lid to be used independently of a lower plate since it eliminates crosstalk.

Preferably, to avoid optical cross-talk, the platen and optical components either are made of or coated with a material opaque to light. Any effective light-absorbing material can be applied over the surface in a layer or film. Examples of useful light-absorbing materials include, carbon and graphite. In some cases, however, the material of the platen may not be entirely opaque at the wavelengths of an interrogative optical beam, hence the underside of the platen may be coated to prevent light leakage and optical cross-talk among the addressable sample volumes within each channel. Alternatively, to prevent optical cross-talk, and help to seal the device to a microplate 23, an elastomer 24 or other material can be located on the second or under surface 14 of the platen around each collection structure.

C.—Methods of Use

According to the invention, the method for detecting a signal from an analytical sample comprises: a) providing a device having a collector structure a capillary channel, along its central axis, containing a light emitting sample in a liquid medium, as described above; b) providing or introducing a volume of liquid sample containing analytes into at least one of the capillary channels; c) optionally, introducing an electromagnetic wavelength into the capillary channel to induce an emission of optical signal from the analyte; and d) detecting said optical signal emission.

The present device may be constructed as modular units, in terms of each individual collector, or in groupings of collectors. An array of collectors and capillary channels may be configured in a variety of ways. As envisioned, the present device may be used in at least two formats, either with or without a traditional well plate depending on the type of assay being performed. That is, the device would be used either as a cover lid for a multi-well microtiter plate of a standard configuration or as a stand-alone device.

According to the first embodiment, individual collectors are situated preferably in a rectilinear grid, spaced on-center to correspond with the wells of a microplate of industry-standard dimensions (e.g., 96, 384, 1536 well matrix) and other irregular configurations. When used as a lid for a microtiter plate, assay reaction components can be dispensed into microplate wells as usual. Each collection structure is inserted into a corresponding well 21 of the plate 23 containing a fluid or aqueous assay solution, such as in FIG. 12. The embodiment illustrated in FIG. 1, for example, is tailored to nest within a 96-well plate. The solutions are drawn up the capillaries if the tip of the projection is in contact with the solution. When using a solution of very low fluid volume, one may wish to compress the device against the microplate 23 to ensure each collector and capillary 16 contacts the solutions and fills the capillary. In such situations, an elastomeric layer 24 that is situated against the second or lower surface 14 of the platen 10 may be favored.

Alternatively, according to a second embodiment, the device can be used independently of the microtiter well plate. If an upper opening for a capillary extends through to the first or upper surface of the platen, fluids or reagents can be dispensed directly into the capillary from the top of the platen, enabling the device to be used in likewise fashion but without a microplate. In a hybrid technique, one may first prepare a well plate with solution or samples, insert the collector and capillary end into the sample, then remove and read the signal separate from the well plate.

In either embodiment, fluid in the capillary can be emptied or forced out using vacuum, centrifugation, or air pressure. The capillaries can then be readily refilled in a short time, and the desired assay procedure may be repeated. Conventionally, entrapment of air bubbles is also problematic in small diameter wells. This issue is not a problem in the present device since a capillary can be open at both ends. When solution fills the capillary, air will be displaced out through the opposite end.

Due to a rather small surface area of exposed liquid within the capillary, the device can reduce surface evaporation from within the wells by up to about eight, ten, or fifteen times, preferably at least an order of magnitude, relative to conventional microplate designs with wide open wells in which the device is not used. The device is designed such that a fluid (e.g., aqueous solution) will spontaneously fill the capillary with volumes in the microliter or submicroliter range. For instance, the evaporative surface area for the present capillary device would be roughly five times lower than that for a well in a standard 1536-well plate. If a multi-capillary devise is used as a lid in a standard plate, the lower opening of the capillary will in effect be covered, reducing evaporation further.

Since the dimensions of wells in a 96-well plate is roughly 6.5 mm wide by 12 mm deep, in a 384-well plate is roughly 3.25 mm wide by 12 mm deep, and in a 1536-well plate is typically 1.7 mm wide by 5.5 mm deep, specific dimensions for collectors may vary according to the requisite optical geometry and use, or the particular design needs of the collectors and capillary channels. The distance that the extremis or tip of a collector structure is maintained from the bottom of a well depends on the volume of the well and is therefore not a critical value, but likely would not be closer than about 0.5–1 mm and may likely be further away.

The dimensions provided herein are only illustrative of representative embodiments and not necessarily limiting. Generally, the thickness of the platen may be on the order of about 0.5–5 mm, up to about 10 mm, preferably about 0.75–4 mm, more preferably about 1 mm to 2 or 2.5 mm. Each collector structure may have a length L, such as in FIG. 5A, up to about 10–12 mm, preferably up to about 2–9 mm, more preferably about 2–5 mm. Capillary channels have a characteristic diameter on the order of less than or equal to about 1500 µm, preferably about 750 µm. Preferably the interior diameter of a capillary is about 20 or 25 µm up to about 500 or 550 µm; more preferably, about 40 µm to about 200 µm. Thus, the volume of each capillary channel is on the order of about $10^{-6}$ cm$^3$ or greater. For example, as will be discussed further below, in the case of a frustoconical configuration, the collector projection can be about 4 mm in length with a capillary of about 5 mm, with a millimeter within the planar support section. This kind of design lets the capillary draw fluid from near the bottom of a well plate. If the collector has an orthogonal parabolic reflector (OPR) design, then the projection, for instance, could be about 1.5–4.5 mm with a capillary on the order of 1–4 mm long or so for a 1536 well plate. Since the center to center distance for a 1536 is about 2.25 mm, the capillary and collector structure would be no wider than that. For a 384-well plate the center to center is 4.5 mm and for a 96-well plate the distance is about 9 mm center to center.

According to certain embodiments, which have the collection structure adapted to engage with the first or upper surface of the platen, two of the present inventive devices may be stacked one on top of another. According to an embodiment, preferably, the interface surface between the two plates is very flat and smooth. The lower openings of the capillary channels in the plate on top can be configured to align and mate with the upper openings of corresponding capillaries in the plate underneath. Through capillary action, sample fluid from the first plate, either the one above or below, can be transferred to the second plate. This feature can facilitate mixing of sample volumes between each capillary.

D.—Potential Applications

The invention, according to an embodiment, provides a multi-capillary platform for high through-put screening that can be used for low volume assays to reduce evaporative loss while increasing detection signal levels. The present invention may be employed for any kind of biological or chemical assay, which can be done in a microplate, and/or that can be aspirated into a capillary.

The types of assays done in microplates are numerous. For instance, in heterogeneous or solid-phase assays, one of the reaction components is immobilized on the surface of a substrate, such as the bottom or walls of a microplate. In the present situation, instead of immobilizing a reaction component on the microplate, biological molecules could be immobilized to the interior of the capillary. The immobilized biomolecule probes usually captures other target components in the reaction solution or mixture. As alluded to above, specific chemistries can be applied to the capillary surface, such as hydroxysuccinimide groups, which bind amine moieties on biomolecules. These amine groups can be found on any protein. When using a microplate in conjunction with the present device, for example, a specific, purified antibody could be immobilized to the capillary. A cell lysate could be in the well of the microplate. Once the capillary is placed in the well, some of the lysate is drawn into the capillary. After a wash step, one of the methods of detection known in the art could be employed to establish the presence of an antigen captured from the lysate. In another example, biomolecules can also be synthesized with specific tags, such as 6 histadine amino acids. This "6×HIS" tag can be captured through it's affinity for nickel ions. Nickel can be incorporated into chelate structures that are applied to the interior surface of the capillary for the capture of "6×HIS" tagged biomolecules.

The present device can also work well with one of the more common methods to detect a reaction (such as a binding event) that involves using fluorescently labeled molecules, such as fluorescence resonance energy transfer (FRET), or sometimes referred to as a homogeneous time-resolved fluorescent assay (HTRF). A target molecule often is, but not always, labeled with a fluorescent moiety (also called a "fluorophore" or "chromophore"). The target binds with a complementary probe. After a light beam of an appropriate wavelength excites the chromophore, fluorescence is detected at the emitting wavelength. If the assay is homogeneous, the possibility of using two labeled reaction components exists to compensate for unbound excess labeled ligands in solution. In a reaction, where two components are both labeled, light of an appropriate wavelength is used to excite one of the chromophores. The emission from the first chomophore is predetermined to be at a wavelength necessary to excite the second chromophore if the two chromophores are in close enough proximity (roughly about 75 angstroms). The emission of the second chromophore is the signal detected by the instrument. Biomolecules can also be made labeled with radioactive isotopes. The decay of the radioactive tag can be detected if a scintillant is in the reaction mix on a bead, coating, or molded into the polymer material of the device.

One can also use the present device to perform enzymatic detection of biomolecular interactions. Specific enzymes can catalyze a chemical change that leads to luminescence, or a color change in the reaction, depending on the type of assay. Luminescence is detected without the need for excitation. Color is detected as a change in the absorbance of a fluid, measured along a certain path-length, at a specific wavelength.

E.—Design Examples

The optical problem to address is determining the size and shape of the collection structure in order to maximize light collection to a detector. A variety of different geometric configurations may be incorporated in the design of the present device, according to methods to enhance the signal detected from fluorescence within capillaries. For instance, the collection structures may have a conical or frustoconical shape, such as the schematic representation of FIG. 11 or 12 illustrates. An elliptical or parabolic geometry, however, is more preferred, such as shown in the various other figures herein. Parabolic collectors or reflectors can be categorized into three types. They include: so-called simple parabolic reflectors (PR), compound parabolic concentrators (CPC), and orthogonal parabolic reflectors (OPR). PRs tend to maximize net signal power emitted and received at a point, whereas CPCs tend to maximize net signal power emitted and received over an area, and OPRs tend to maximize net signal power emitted and received over a line. Preferred geometries for parabolic collector forms are described in U.S. Pat. No. 3,899,672 (Levi-Setti); U.S. Pat. No. 3,923, 381 (Winston); U.S. Pat. No. 4,003,628 (Winston); U.S. Pat. No. 4,173,778 (Snavely et al.); U.S. Pat. No. 5,037,191 (Cheng); or U.S. Pat. No. 5,235,470 (Cheng), the contents of each is incorporated herein by reference.

As discussed in detail in U.S. Pat. No. 5,037,191, or U.S. Pat. No. 5,235,470, FIG. 3 illustrates the capability of an orthogonal parabolic reflector system to collect light emission from a linear source. Curved surface 30 depicts the solid body of the orthogonal reflector, which is truncated by the necessary sections only, relative to the position of the capillary line source or sink 31, and has a rotational or reflective surface 34. The resultant focal point F at 32 concentrates the energy emitted from the line or cylindrical radiation source onto the focal point F32. At the focal point F32, the radiation appears to have no apparent dimensions, and the equal distance from the focal point reflected to the axis is unique of the orthogonal parabolic mirrors. If the light source emits a coherent radiation, then at the focal point in all angles, the light also will be emitting as a coherent point source. Due to the fact there is no material present at the focal point F32, there is no material limitation in terms of the physical size and energy density or flux densities. Due to the apparent dimensionless property, the spatial filter located at that focal point will not reduce the intensity of the radiation source. This is another one of the breakthroughs of using an OPR in addition to the capability of increased intensity. This property will enable the light to be emitted with excellent beam quality.

Figure 4:
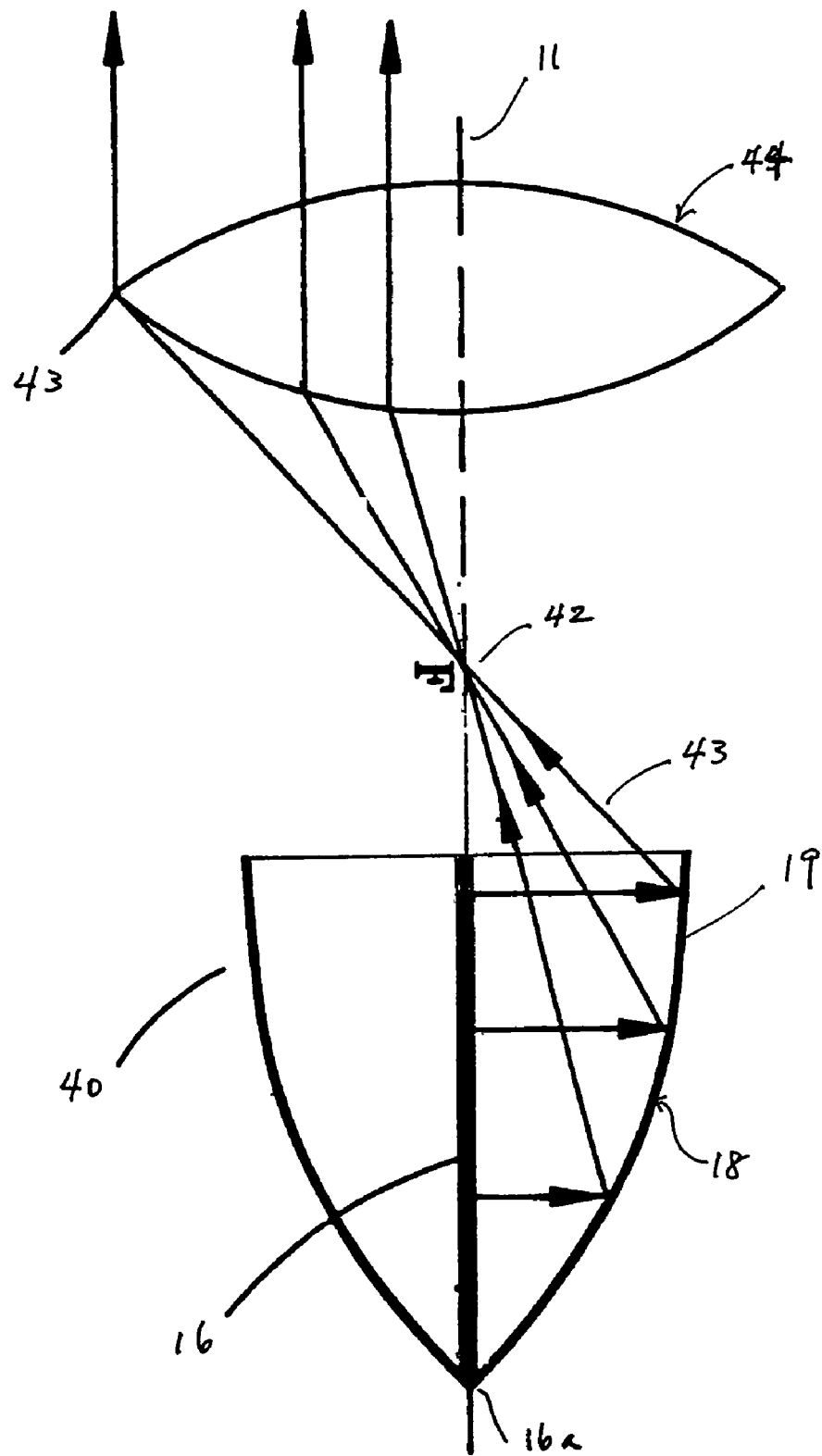
FIG. 4 depicts in cross-section, a collection structure with an associated optical element, which according to the embodiment illustrated is a collimator lens.

FIG. 4 illustrates an embodiment of a collector unit 40 with an orthogonal parabolic geometry and optical lens 44, which would have the same focal point F at 42. A number of light rays 43 are redirected by the lens 44. This lens will convert a linearly produced radiation source into a parallel beam.

Figure 5B:
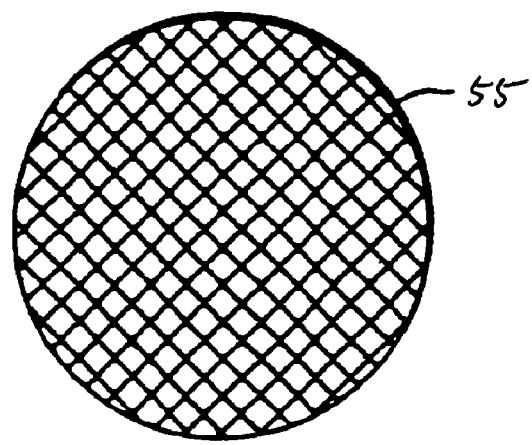
FIG. 5B represents a light flux spot that is projected from the embodiment in FIG. 5A.
Figure 5A:
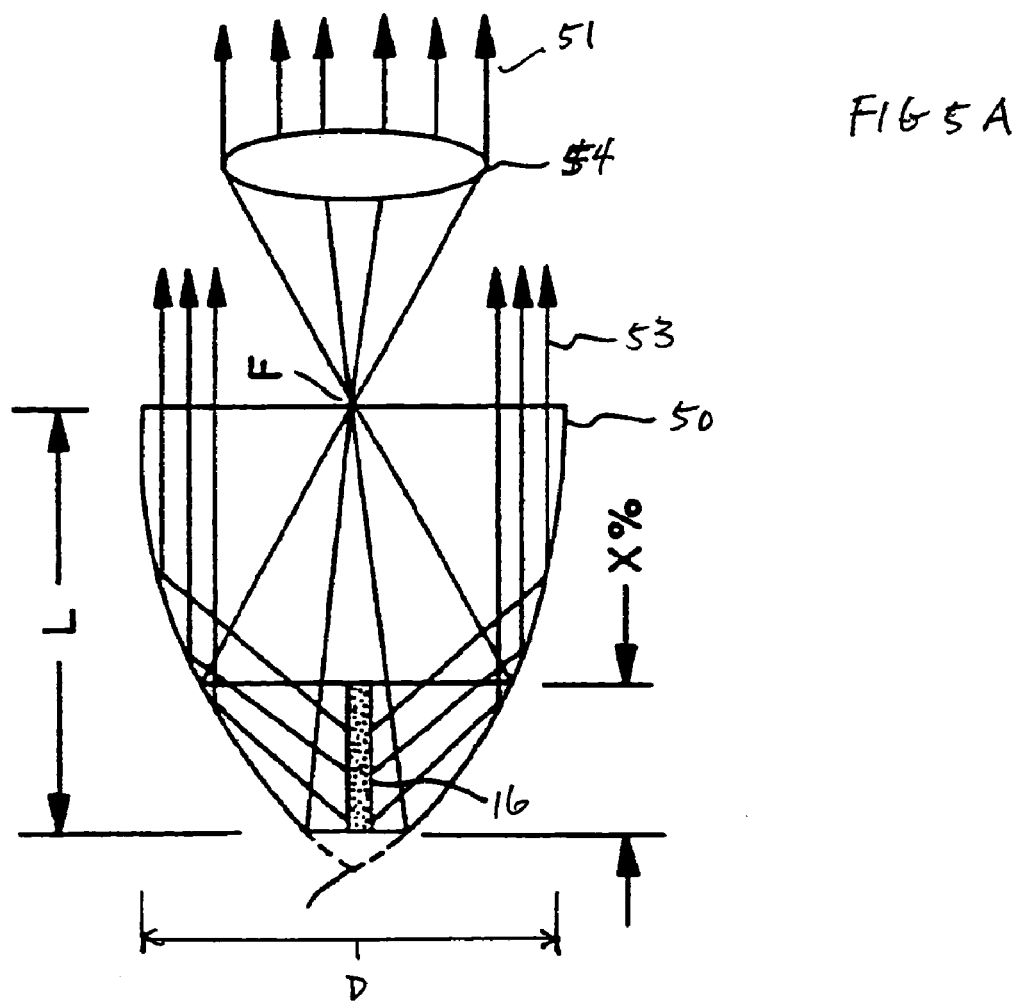
FIG. 5A depicts in cross-section, a variation of the embodiment shown in FIG. 4.

FIG. 5A illustrates a variation of the design in FIG. 4. Reflector 50 has a diameter D at its large open end or aperture, and a length which is L. The reflector envelopes a central capillary and emission source 16. The light intensity in the axial direction of the image illustrated at FIG. 5B can be augmented by using a lens 54 to make parallel the rays forming the primary image at focal spot F, i.e., to produce additional parallel rays 51. These parallel light rays 51 together with the peripheral parallel rays 53, produce a uniform and intense light beam having a circular cross-section or a circular flux image 55. The distribution of light intensity in beam or flux image 55 can be changed by changing the portion of the axial distance of L occupied by emission source 16. The length of capillary 16 is a percentage (X %) of the total length L of the collection structure. Precise dimensions should be tailored to meet specific applications for the best transmission results.

Figure 6:
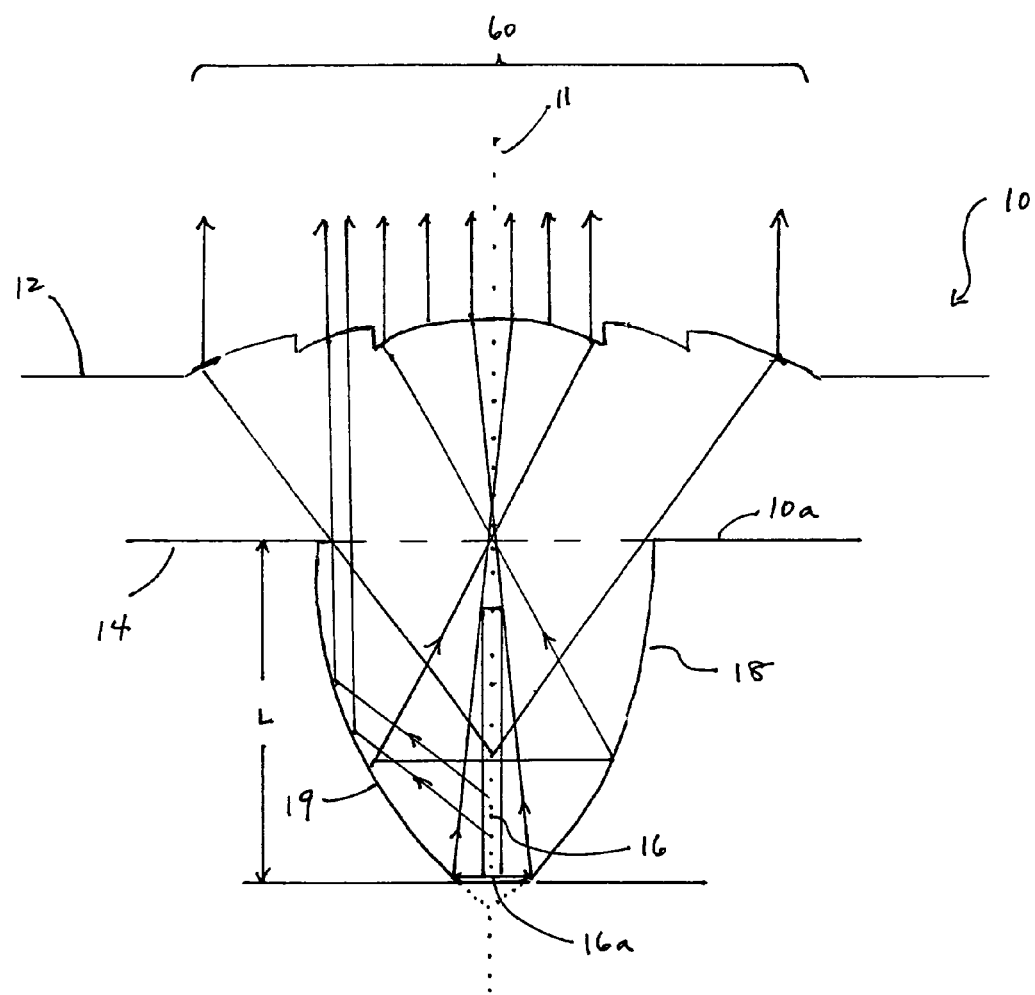
FIG. 6 depicts a variation of the embodiment shown in either FIG. 4 or 5A, in which a fresnel-type lens having varying focal lengths is situated on the first surface of the planar structure as part of the collection structure to collimate optical emissions from the capillary.

A variation on the configuration of FIG. 5 is illustrated in FIG. 6. FIG. 6 shows an embodiment with a fresnel lens 60 of varying focal lengths to maximize collection of stray light beams. The lens is integrated within the upper surface 12 of the platen structure 10, and the collector extends from and forms part of the lower surface 14.

Figure 7A:
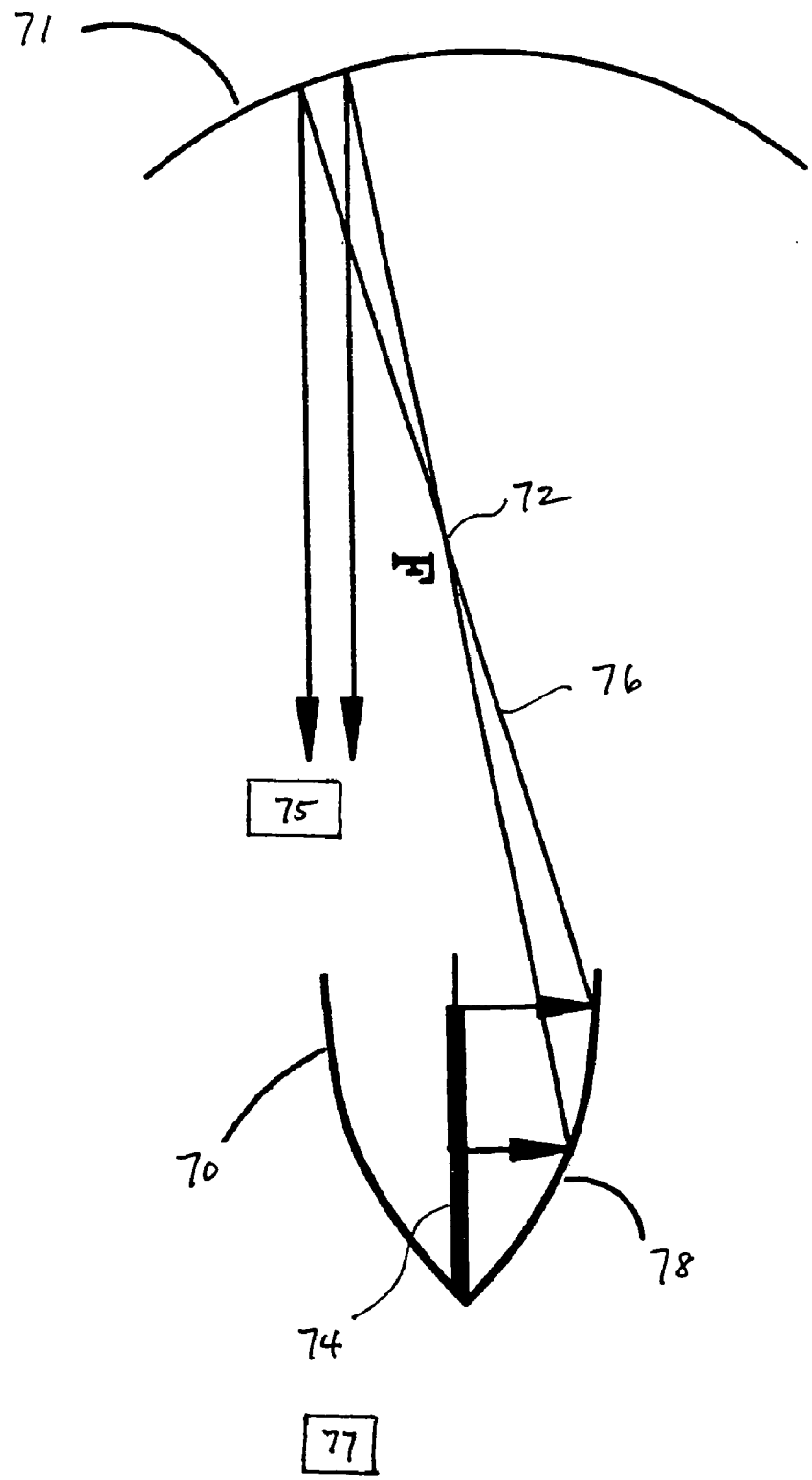
FIG. 7A depicts a schematic representation of an alternative embodiment in which a reflector is used to direct optical emissions from the capillary toward a detector situated below the collection structure.
Figure 7B:
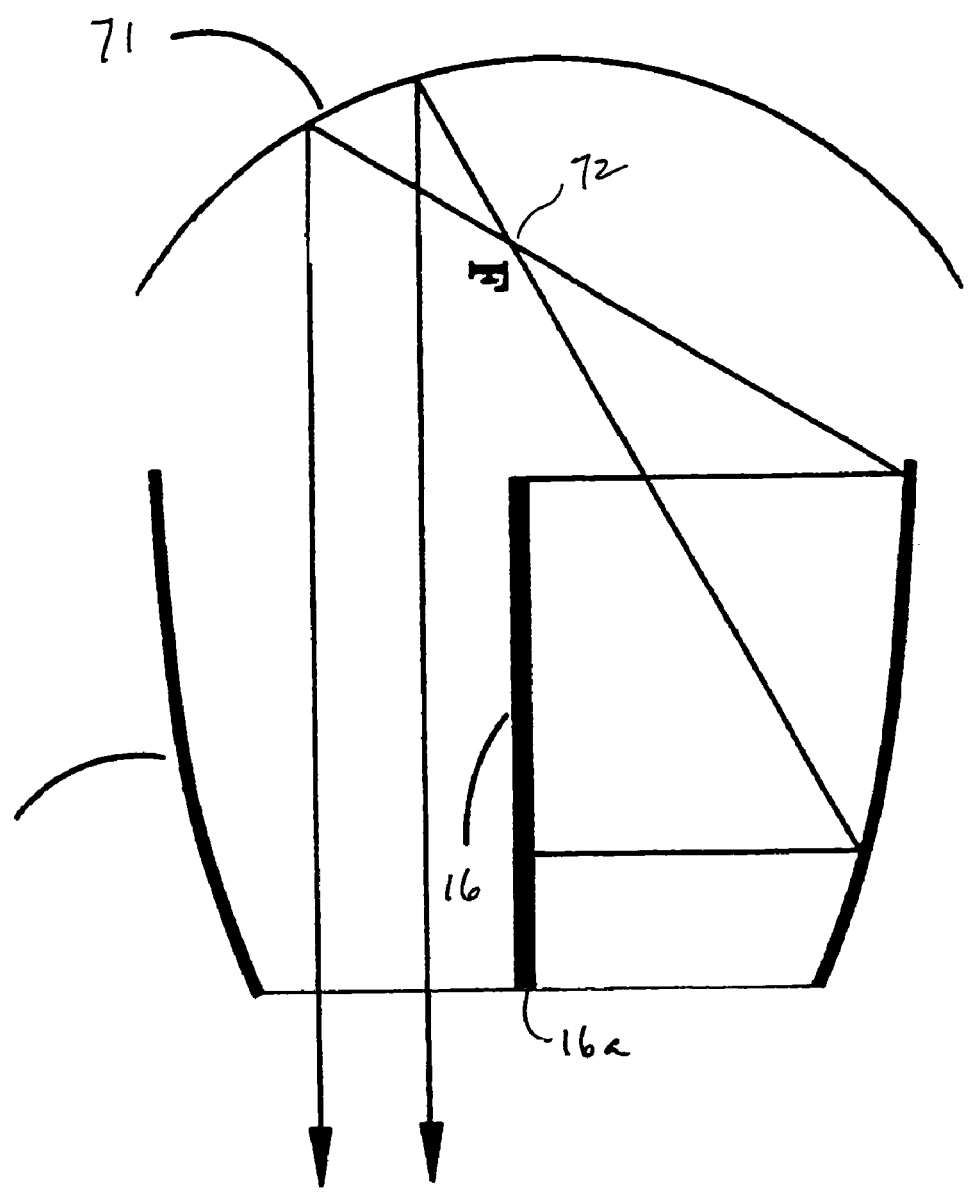
FIG. 7B depicts a schematic representation of a variation of the embodiment shown in FIG. 7A.

FIG. 7A depicts another configuration in which the collection structure is used with a parabolic reflector 78. The parabolic reflector shares the same focal distance of focal point F at 72 with the orthogonal parabolic reflector geometry. The collection structure in the form of an orthogonal parabolic reflector is shown as 70; the capillary linear source as 74; the optical rays as 76; and the reflective surface of the collector as 78. The light rays reflected from the parabolic reflector 71 may be collected by a detector device situated either between collection structure 70 and parabolic reflector 71 at position 75, or underneath collection structure 70 at position 77, depending on the configuration of the detection system. A signal receive by the detector is subsequently processed and analyzed. A scanner or a digital imager can be used. FIG. 7B illustrates a variation of a collection structure in the form of a compound orthogonal parabolic reflector with an ordinary parabolic reflector 71 sharing the same focal point F at 72. Optical energy emitted from capillary 16 is reflected towards the parabolic reflector 71, and out the bottom.

Figure 8:
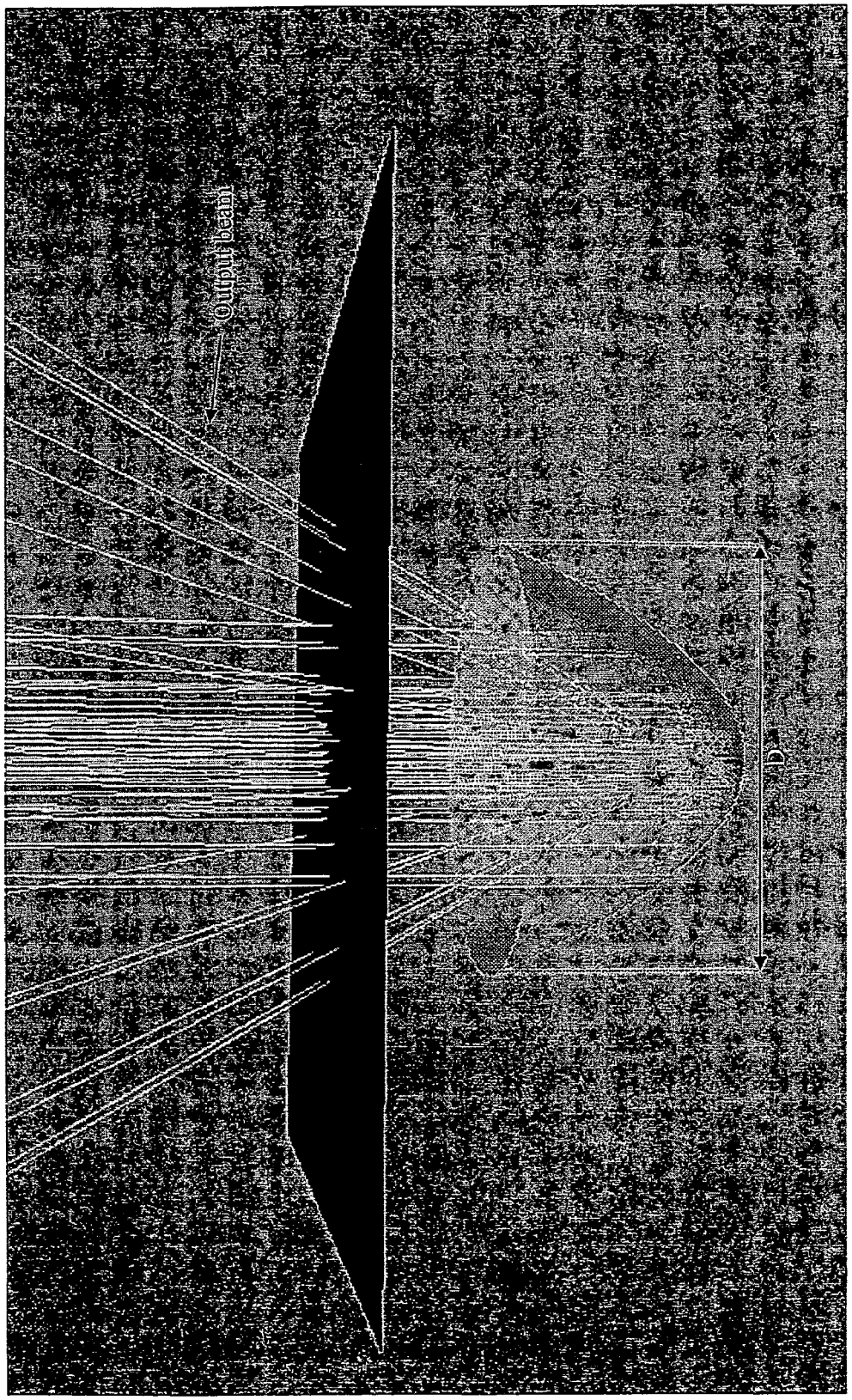
FIG. 8 depicts computer generated ray tracing for a paraboloid collection structure.

FIG. 8 is an image of a three-dimensional computer-generated paraboloid with rays. The equation of the three-dimensional parabola is:

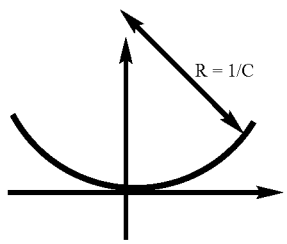

$$Z = \frac{Cr^2}{1 + \sqrt{1 - (1 + \varepsilon)C^2 r^2}}$$

with $\varepsilon = -1$. As an example, the flux density upon a detector is calculated, using Apilux 2.0 software, for a cylindrical linear source (diameter≈1.8 mm, length≈5 mm, isotropic). The rays that are reflecting on the paraboloid are collimated (center of the output beam 81). FIG. 9 shows the irradiance distribution on a screen of a detector 93. A change in the value of the radius of curvature R, from 2 mm to 7 mm, causes an increase in the calculated percentage of flux received on the detector relative to the source flux, when using a reflector having a length L of 6 mm, and a diameter D. The results are summarized in Table 1.

TABLE 1

| Example | Radius of Curvature | Diameter, D | Transmitted Flux |
|---------|--------------------|-------------|--------------------|
| 1 | R = 2 mm | 10 mm | 73% |
| 2 | R = 3 mm | 12 mm | 83% |
| 3 | R = 4 mm | 14 mm | 90% |
| 4 | R = 5 mm | 15 mm | 95% |
| 5 | R = 6 mm | 17 mm | 97% |
| 6 | R = 7 mm | 19 mm | 99% |

The parabolic geometry affords good light collection properties when R>7 mm. The diameter of aperture the collection structure near the top or first surface of the planar support is also relatively important. With embodiments incorporating a parabolic or an orthogonal parabolic shape, the radius of curvature should be as large as possible. Hence, preferably the diameter D is ≧19 mm or 25 mm. The area at the bottom of the collection structure and the bottom of the capillary is not particularly sensitive. About 1 mm is a corrective value. The surface roughness of the reflector/mirror should be preferably as smooth as possible on the end of the parabola near the top of the planar support structure.

Figure 10:
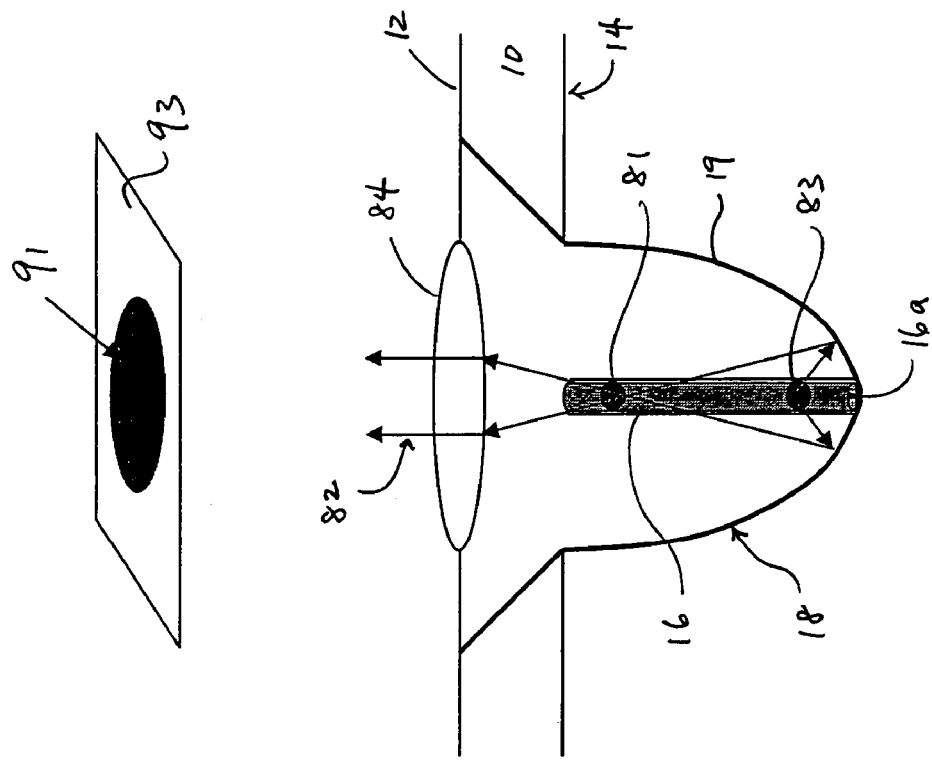
FIG. 10 is a schematic representation of another embodiment of the collection structure having an elliptical shape. The elliptical shape of the collection structure projects an optical emission or a light flux form the capillary within onto a detector or screen.

FIG. 10 shows an alternate, elliptical design having two foci 81, 83, and lens 84. In this case: $-1 < \varepsilon < 0$. When $\varepsilon$ is near to $-1$, the diameter of the collection structure is near to that of the paraboloid shape, but the flux is 20% less. When $\varepsilon$ is near to 0.5, the diameter of the collection structure is smaller (D=16 mm vs. 19 mm, with $\varepsilon=-0.5$, and R=7 mm) but the flux is 30% less. Hence, with elliptic shape, the diameter (D) of the aperture may be more compact than that for a parabolic design, but the optical flux would decrease deeply and one would need to add a lens or a spherical or aspherical diopter to direct and collimate the rays 82. A light flux or irradiance distribution 91 is projected on to a screen of a detector 93.

FIG. 11 depicts in cross-section, an embodiment with at least three conically-shaped collection structures side by side. Each collection structure is connected with its adjacent structure by the platen 10. The platen had to avoid optical cross-talk the platen can be fabricated from a material that does not transmit light, or preferably, has an optically non-transmissive coating. According to the embodiment, as illustrated, one may apply an elastomeric layer 24 on either the top 12 or bottom 14 surfaces, preferably on the lower surface. A capillary channel 16 in each collection structure extends through an optical element 90, like a lens. A light flux from within the capillary is projected onto a detector like in FIG. 10.

FIG. 12 depicts the inventive device according to FIG. 11 engaged with a microplate 23, wherein each collection structure 15 is inserted into a corresponding well 21 of the microplate.

Figure 13:
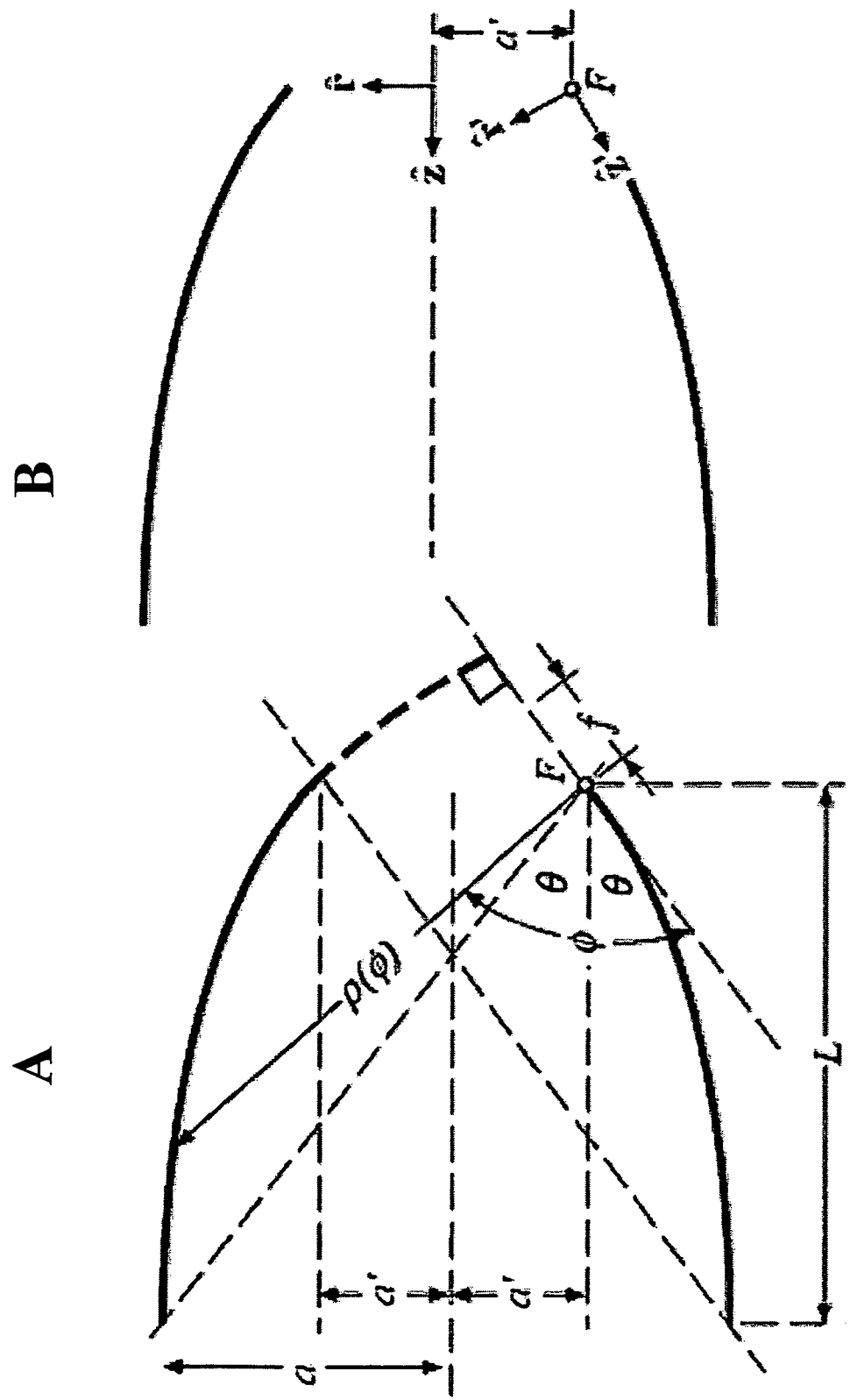
FIG. 13 is a schematic representation of another embodiment of the collection structure having a so-called "Winston Cone" light concentrator shape. The Winston cone may be employed to channel light wavelengths, according to an embodiment of the present invention.

Certain embodiments of the present device may have the geometry of a Winston cone. FIGS. 13A and 13B show diagrams of a Winston cone. A Winston cone is an off-axis parabola or revolution designed to maximize collection of incoming rays within some field of view. (Hildebrand, R. H., Erratum to "Throughput of Diffraction-Limited Field Optics System for Infrared and Millimetric Telescopes," *Appl. Opt.* 24, 616, 1985; Hildebrand, R. H. and Winston, R., "Throughput of Diffraction-Limited Field Optics System for Infrared and Millimetric Telescopes," *Appl. Opt.* 21, 1844–1846, 1982; Welford, W. T. and Winston, R., *High Collection Nonimaging Optics*, San Diego: Academic Press, 1989; Winston, R., "Light Collection within the Framework of Geometric Optics," *J Opt. Soc. Amer.* 60, 245–247, 1970.) As an example of a non-imaging light concentrator, Winston cones can funnel all wavelengths passing through an entrance aperture and out through an exit aperture. They maximize the collection of incoming rays by allowing off-axis rays to make multiple reflections before passing out the exit aperture. Certain families of off-axis rays, which are rejected back out the entrance aperture, could be useful for detection systems using at least two different wavelengths. In addition, since diffraction effects become important for radiation wavelengths similar to the cone's physical dimensions, Winston cones exhibit a waveguide-like cutoff at low frequencies. In FIG. 13A, the entrance and exit apertures are of radius a and a', respectively. F is the focus of the upper parabola segments, and f is its focal length. The length of the cone is L. FIG. 13B, on the right, shows the origins and orientations of the focus-centered and symmetry axis-centered coordinate systems.

The present invention has been described in general and in detail by way of examples. Persons skilled in the art understand that the invention is not limited necessarily to the specific embodiments disclosed. Modifications and variations may be made without departing from the scope of the invention as defined by the following claims or their equivalents, including equivalent components presently known, or to be developed, which may be used within the scope of the present invention. Hence, unless changes otherwise depart from the scope of the invention, the changes should be construed as being included herein.

We claim:

1. A device for performing an assay or detecting an optical signal from an analytical sample, said device comprising: a number of collection structures; a capillary channel, adapted to contain a sample volume, running length-wise along an axis substantially parallel with a major axis of each collection structure; and each collection structure having a shape effective to either concentrate or direct an optical signal from said capillary channel towards said detector wherein said device further comprises a planar structure with a first surface and a second surface; said planar structure is situated across said major axial end of said collection structures, which extends in an orthogonal fashion from said second surface.

2. The device according to claim 1, wherein each of said collection structure has a geometry which is adapted to project an optical signal emitted from an analyte in said sample volume towards said detector by means of reflection.

3. The device according to claim 2, wherein said geometry of said collection structure has a major and a minor axial end.

4. The device according to claim 1, wherein said device further comprises a number of optical elements located on said first surface or within said planar structure, each corresponding to a collection structure and centered on said capillary channel.

5. The device according to claim 4, wherein said optical element is a collimator, which directs said optical signal towards a said detector positioned above said first surface.

6. The device according to claim 4, wherein said optical element is a reflector that directs said optical signal towards said detector situated below each of said collection structures.

7. The device according to claim 4, wherein said optical element is a lens or microlens.

8. The device according to claim 4, wherein said device further comprises either an array of lenses or microlenses, a fresnel lens or fresnel lens of varying focal lengths, a grating, or a surface-relief diffuser.

9. The device according to claim 2, wherein said geometry of said collection structure incorporates a surface, generated by rotating about an axis, which is part of at least one of the following: a cone, an ellipse, or a parabola.

10. The device according claim 9, wherein a radius of rotation is either of a fixed length or a variable length.

11. The device according to claim 1, wherein said collection structure has a mirrored surface.

12. The device according to claim 1, wherein said collection structure has a reflecting surface which has an axis and is open at least at one axial end and, in an axial section generally conforms to an axial section of a surface that is generated by rotating a portion of a parabolic curve about an axis perpendicular to the axis of the parabola defined by said curve.

13. The device according to claim 12, wherein said capillary channel forms an elongated source or sink which extends at least in the direction of said axis of said reflecting surface and is at least partially enveloped by said reflecting surface.

14. The device according to claim 1, wherein said axis of said capillary channel is co-axial with said collection structure.

15. The device according to claim 1, wherein said capillary channel has a first opening located at said first surface, and extends through said collection structure to a second opening at a terminus of said collection structure.

16. The device according to claim 1, wherein said device is used for non-imaging optical applications.

17. The device according to claim 1, wherein said collection structure is made of a transparent material having an index of refraction greater than that of said sample volume in said capillary channel.

18. The device according to claim 1, wherein said device is adapted for use in conjunction with a microtiter well plate, and each collection structure nests within a well of said plate.

19. The device according to claim 17, wherein when said device is adapted for use in conjunction with a microtiter well plate containing fluid solution, said fluid solution fills said capillary channel.

20. The device according to claim 18, wherein surface evaporation from within said microtiter plate wells is reduced by up to about 15 times relative to when not using said device.

21. The device according to claim 1, wherein each capillary channel has a sidewall surface functionalized with predetermined properties.

22. The device according to claim 1, wherein said device is used for biological or biochemical assays involving fluorescence.

23. The device according to claim 1, wherein said device is used for monitoring cell culture functions.

24. A device for analyzing a biological or chemical sample, said device comprising:
 a) a planar structure, with a first surface and a second surface;

b) a number of collection structures extending in a generally orthogonal fashion from said second surface;
c) a capillary channel, adapted to contain a sample volume, running along an axis substantially parallel with a major axis of each collection structure; and
d) each collection structure having a geometry adapted to collect or direct an electromagnetic radiation signal from said capillary channel towards a detector.

25. The device according to claim 24, wherein said geometry of each collection structure is adapted to reflect said signal.

26. The device according to claim 24, wherein said device further comprises a number of optical elements located on said first surface or within said planar structure, each optical element corresponding to a collection structure and centered on said capillary channel.

27. A method for detecting a signal from an analytical sample, said method comprising:
a) providing a reflective device for collecting and directing an electromagnetic signal from a capillary channel, adapted to contain a sample volume;
b) aligning length-wise said capillary channel substantially parallel with a major axis of rotation of said reflective device;
c) providing an analyte in said sample volume;
d) introducing an electromagnetic wavelength into said capillary channel to induce an emission of signal from said analyte;
e) directing said emission of signal toward a detector; and detecting said signal; and placing said reflective device in a well of microplate containing fluid solution, and filling said capillary channel with said solution.

28. The method according to claim 27, further comprises projecting said optical signal toward a said detector positioned above said first surface.

29. The method according to claim 27, further comprises directing said signal toward said detector situated below said reflective device.

30. The method according to claim 27, further comprises providing a functionalized surface with predetermined properties to a sidewall surface of said capillary channel.

31. The method according to claim 27, further comprises using said device for non-imaging optical applications.

32. The method according to claim 27, wherein said method reduces surface evaporation from said microplate well by up to about 10 or 15 times relative to an amount of evaporation in a microplate not using said device.

33. The method according to claim 27, further comprises interacting said optical signal with a number of optical elements located either with a planar structure or on a first surface of said planar structure, wherein each optical element or array of elements corresponds to a collection structure and centered on said capillary channel.

* * * * *